(12) United States Patent
Miric et al.

(10) Patent No.: US 6,346,420 B1
(45) Date of Patent: Feb. 12, 2002

(54) METHOD OF ANALYZING A GAS MIXTURE TO DETERMINE ITS EXPLOSIBILITY AND SYSTEM FOR IMPLEMENTING A METHOD OF THIS KIND

(75) Inventors: Tomislav Miric, Nanterre (FR); Evgenij Karpov, Moskovska Oblast (RU); Boris Basovski, Moscou (RU); Evgenij Dikolenko, Moscou (RU); Aleksandar Petrov, Moscou (RU)

(73) Assignee: Oldham France S.A., Arras (FR)

( * ) Notice: Subject to any disclaimer, the term of this patent is extended or adjusted under 35 U.S.C. 154(b) by 0 days.

(21) Appl. No.: 09/512,837

(22) Filed: Feb. 25, 2000

(30) Foreign Application Priority Data

Feb. 25, 1999 (FR) .............................................. 99 02374

(51) Int. Cl.[7] .......................... G01N 33/22; G01N 27/14; G01N 27/16
(52) U.S. Cl. ........................ 436/143; 436/141; 436/142; 436/151; 422/94; 422/95; 422/96; 422/97; 422/98; 73/23; 73/21; 73/23.31; 73/25.01; 73/25.05; 73/31.05
(58) Field of Search .............. 422/94–97; 436/141–143, 436/151; 73/23.21, 23.31, 31, 25.01, 25.03, 25.05, 31.05

(56) References Cited

U.S. PATENT DOCUMENTS

| | | | |
|---|---|---|---|
| 3,607,084 A | * | 9/1971 | Mackey et al. .............. 436/143 |
| 3,960,495 A | * | 6/1976 | Tantram |
| 4,314,475 A | * | 2/1982 | Karpov et al. |
| 4,538,448 A | * | 9/1985 | Boutonnat et al. |
| 5,070,721 A | | 12/1991 | Tantram |
| 5,311,447 A | * | 5/1994 | Bonne |
| 5,709,792 A | | 1/1998 | Zdanevitch et al. |
| 5,741,413 A | | 4/1998 | Capetanopoulos |
| 5,965,451 A | * | 10/1999 | Plog et al. .............. 436/143 X |

FOREIGN PATENT DOCUMENTS

| | | | |
|---|---|---|---|
| FR | 1506941 | * | 12/1967 |
| FR | FR 2 537 722 | | 6/1984 |
| GB | 2091882 | * | 8/1982 |
| SU | 457915 | * | 2/1975 |
| WO | WO 91/06849 | | 5/1991 |

OTHER PUBLICATIONS

I. E. Birenberg et al, Ugol'1974 49–51.*
A. A. Korzhavin et al, Combustion and Flame 1997, 109, 507–520.*

* cited by examiner

Primary Examiner—Arlen Soderquist
(74) Attorney, Agent, or Firm—Young & Thompson

(57) ABSTRACT

In this method of analyzing a gas mixture containing at least one inflammable gas to determine its explosibility, a resistive heating element (15) is energized in an analysis enclosure (12) communicating with the gas mixture to be analysed to burn the gas mixture in the enclosure, an electrical signal (S) at the terminals of the resistive element (15) is measured during combustion, and the explosibility of the gas mixture is determined from a comparison of values of the signal measured during a transient phase in which the concentration of the inflammable gas in the gas mixture is falling. The measurements taken during the transient phase are taken at times chosen to obtain, for different inflammable gases, substantially identical measurement signals for concentrations corresponding to identical explosibilities.

11 Claims, 2 Drawing Sheets

METHOD OF ANALYZING A GAS MIXTURE TO DETERMINE ITS EXPLOSIBILITY AND SYSTEM FOR IMPLEMENTING A METHOD OF THIS KIND

The present invention relates to a method of analysing a gas mixture containing one or more inflammable gases to determine the explosibility of the mixture.

It also relates to an analysis system for implementing a method of this kind.

A particularly interesting application of the method and system is determining the danger of explosion of a mixture of gas and inflammable vapour in production installations liable to give off inflammable gases, in particular in the chemical, petroleum, mining and gas industries.

There are various prior art techniques for determining the risk of explosion of a gas mixture, in particular by chromatography, mass spectrometry, flame ionization and optical techniques of analysing the mixture.

One of the most widely used techniques, because it is so simple to use, employs two thermochemical elements in a Wheatstone bridge, one of which is active and the other of which has received an appropriate surface treatment to render it incapable of burning the gas mixture.

The thermochemical elements are supplied with electrical energy to heat them to the temperature of catalytic combustion of the or each inflammable gas.

Obviously, the heat of the thermochemical element depends on the heat given off during catalytic combustion and on the supply current.

By comparing the measurement signals from the Wheatstone bridge it is possible to determine the heat given off during combustion, which depends on the concentration of each inflammable gas, its calorific value and its diffusion coefficient, and the explosibility of the gas mixture. Explosibility is generally expressed as a percentage of the lower explosibility limit (LEL).

This type of technique has a number of major drawbacks, in particular because it generates additive errors due to drift with time of the Wheatstone bridge circuit and multiplicative errors due primarily to the different diffusion coefficients of the inflammable gases and their different calorific values.

These errors cause divergences in the response curves for the various gases, i.e. variations of the explosibility measurement signal of as much as 80% for different compositions of the mixtures.

Also, using two thermochemical elements which must be supplied with electrical power considerably reduces the autonomy of the measuring instruments when they are in the form of portable devices.

Attempts have been made to overcome the drawbacks by using only one thermochemical element and determining the explosibility of the gas mixture from a comparison of two measurement signals obtained during a transient phase of combustion during which the concentration of the or each inflammable gas in the gas mixture falls.

This technique considerably limits the power consumption of the measuring instrument and eliminates additive errors.

It does not eliminate multiplicative errors, however.

The object of the invention is to overcome these drawbacks.

It therefore consists in a method of analysing a gas mixture containing at least one inflammable gas to determine its explosibility, including the following steps:

energizing a resistive heating element in an analysis enclosure communicating with the gas mixture to be analysed to burn the gas mixture in the enclosure;

measuring an electrical signal at the terminals of the resistive element during combustion; and determining the explosibility of the gas mixture from a comparison of values of the signal measured during a transient phase in which the concentration of the inflammable gas or gases in the gas mixture is falling;

characterized in that the measurements taken during the transient phase are taken at times chosen to obtain, for different inflammable gases, substantially identical measurement signals for concentrations corresponding to identical explosibilities.

The analysis method of the invention can also have one or more of the following features:

the analysis enclosure has an inlet orifice for the gas mixture calibrated to assure the diffusion of a quantity of gas towards the enclosure during the transient phase which is less than the quantity of gas burned therein;

the measurements are taken at times corresponding to values of the measurement signal from approximately 80% to approximately 40% of the maximum value of the electrical signal at the terminals of the resistive element;

if the gas mixture includes a plurality of inflammable gases having different combustion regimes a cycle of analysing said mixture is performed for each inflammable gas by energizing the resistive element to heat it to the combustion temperature of the gas, measuring the electrical signal and determining the explosibility of the gas mixture, and the result obtained is added at the end of each analysis cycle;

the analysis enclosure communicates with the gas mixture to be analysed via a porous partition.

The invention equally consists in a system for analysing a gas mixture containing at least one inflammable gas to determine its explosibility, for implementing the method defined above, characterized in that it includes an analysis enclosure in communication with the gas mixture to be analysed and having a resistive heating element disposed in the internal volume of the enclosure and a central analysis unit including means for energizing the resistive heating element to heat it to the combustion temperature of the or each inflammable gas, means for calculating the explosibility of the gas mixture including means for measuring an electrical signal at the terminals of the heating element and means for comparing values of the electrical signal at the terminals thereof, and in that the central analysis unit includes means for controlling the operation of the measuring means so as to take said measurements during a transient phase of reduction of the concentration of the or each inflammable gas in the gas mixture, at times chosen to obtain, for different inflammable gases, substantially identical measurement signals for concentrations corresponding to identical explosibilities.

The analysis enclosure advantageously has a gas mixture inlet orifice, said orifice being calibrated to assure the diffusion of a quantity of gas towards the enclosure during the transient phase less than the quantity of gas burned therein.

The analysis enclosure preferably includes a combustion chamber in which the resistive heating element is disposed and an expansion chamber communicating with the gas mixture to be analysed via a porous partition, a separator wall incorporating said calibrated orifice lying between the combustion chamber and the expansion chamber.

Other features and advantages will emerge from the following description which is given by way of example only and with reference to the accompanying drawings, in which:

FIG. 1 shows a gas mixture analysis system 10.

Figure 1:
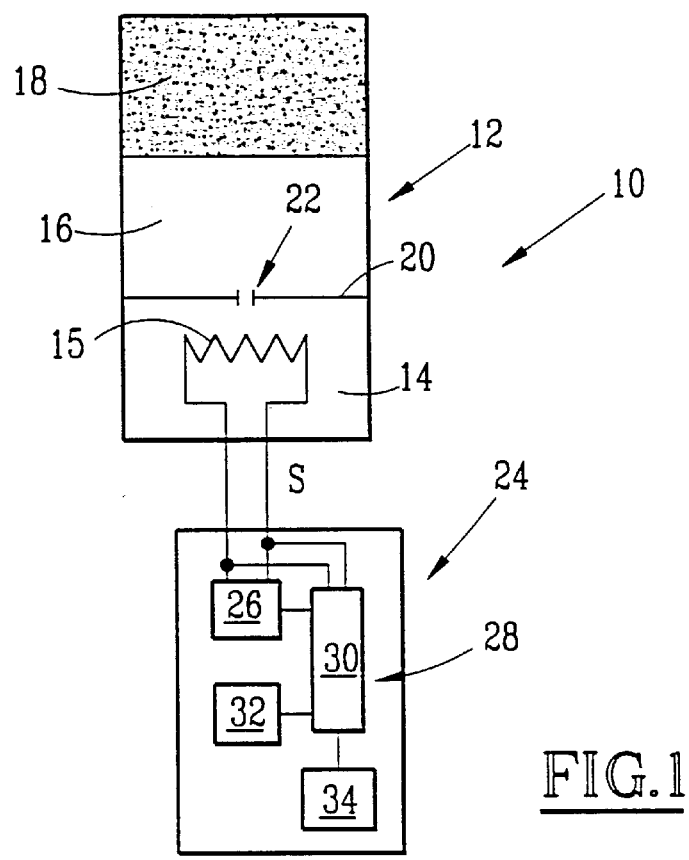
FIG. 1 is a diagram showing an analysis system in accordance with the invention.

It is used to determine the explosibility of a gas mixture contained in an analysis enclosure 12, supplying a result in the form of a percentage of the lower explosibility limit (LEL) or explosivity of the gas mixture.

The enclosure 12 includes a combustion chamber 14 containing a resistive heating element in the form of a filament made from a thermochemical material and an expansion chamber 16 communicating with the atmosphere to be analysed via a porous wall 18 enabling the gas mixture to be analysed to penetrate with little resistance into the expansion chamber 16.

A wall 20 with a calibrated orifice 22 lies between the combustion chamber 14 and the expansion chamber 16.

The dimensions of the calibrated hole 22 are chosen so that the gas diffuses from the expansion chamber 16 towards the combustion chamber 14 by free diffusion of the gas molecules and depends only on the diffusion coefficients of the gas and its concentration gradient.

Similarly, the dimensions of the expansion chamber are chosen to attenuate effectively turbulence from outside liable to interfere with the flow of the gas mixture towards the combustion chamber 14.

The combustion of the gas mixture in the combustion chamber 14 takes place in two distinct stages, namely a transient stage during which the flow of gas through the calibrated orifice 22 is insufficient to compensate the fall in the concentration of inflammable gas due to its combustion, so that the concentration of the inflammable gas in the gas mixture falls in a substantially exponential manner, and a stage corresponding to permanent conditions during which the concentration of inflammable gas remains substantially constant.

The filament 15 is connected to a central analysis unit 24 including an electrical power supply 26 for the filament 15 and means for determining the explosibility of the mixture including means 28 for measuring the electrical signal at the terminals of the filament 15 and in particular its voltage.

The measuring means 28 include a central processor unit 30 consisting of a microcontroller associated with memory means 32 storing an algorithm controlling the operation of the system 10 and data obtained by previous calibration and corresponding to a variation as a function of time of the electrical signal at the terminals of the filament 15 for each type of gas mixture that the system can analyse and a clock 34 operating in conjunction with the central processor unit 30 to sample signals at the terminals of the resistive element 15 at predetermined measuring times.

Under the control of the central processor unit 30, the power supply 26 heats the filament 15 to the combustion temperature of the or each inflammable gas in the gas mixture to be analysed.

Figure 2:
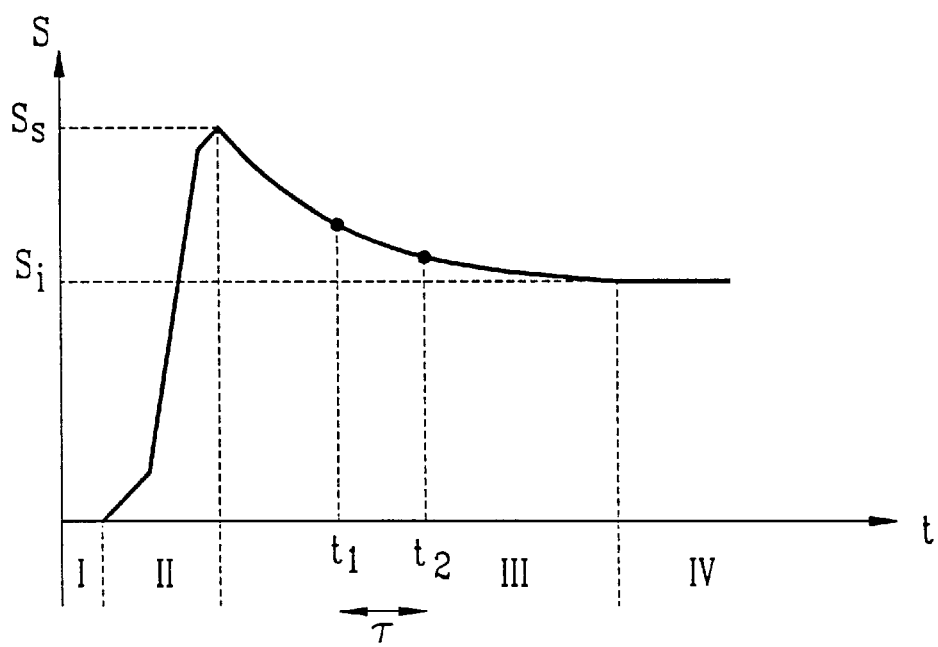
FIG. 2 is a curve showing the variation as a function of time of the measurement signal at the terminals of the resistive heating element.

Referring to FIG. 2, after voltage is applied to the filament 15, the signal S at the terminals of the filament 15 remains at a zero level for a short time period corresponding to the reaction time of the system (phase I). As soon as the gas mixture starts to combust, the output signal S, which is proportional to the temperature of the filament 15, rises quickly to a maximum value Ss (phase II).

In the next phase III the flow of gas through the calibrated orifice 22 is insufficient to compensate the drop in the concentration of inflammable gas and as a result the signal S, which is dependent on that concentration, falls in a substantially exponential manner to a value Si corresponding to an equilibrium value.

The signal S remains constant during the next phase IV, which corresponds to a phase of equilibrium between the quantity of inflammable gas burned and the quantity of inflammable gas entering via the calibrated orifice 22.

Note that the signal S shown in FIG. 2 corresponds to the sum of individual signals generated by each inflammable gas in the gas mixture to be analysed, the individual signals varying independently of the signals generated by the other inflammable gases.

The change in concentration during the previously mentioned phase III is used to determine the explosibility of the gas mixture.

During this phase, the change of concentration can be interpreted using a model based on an analogy with a dynamic system acted on by two forces, namely an inertial force $F_i$ and a damping force $F_a$ respectively represented by the following equations:

$$F_i = -K d^2C/dt^2 \tag{1}$$

$$F_a = -b dC/dt \tag{2}$$

in which K and b respectively represent the inertia and damping constants of the dynamic system and C represents the concentration of inflammable gas in the combustion chamber.

This system of two forces complies with the following differential equation:

$$d^2C/dt^2 + \delta dC/dt = 0 \tag{3}$$

in which:

$\delta = b/K$, represents the damping factor of the system.

The solution of the differential equation (3) follows an exponential curve to base e which varies as a function of time and complies with the equation:

$$C = Cs[r + (1-r)e^{-t/T}] \tag{4}$$

in which:
- r=Ci/Cs corresponds to the coefficient of reduction of the inflammable gas concentration in the combustion chamber,
- T=1/δ, designates the time constant of the system, and
- Ci and Cs respectively correspond to the inflammable gas concentration in the combustion chamber at the equilibrium points Si and at the point corresponding to the maximum signal Ss.

Note that for low inflammable gas concentrations the value of the signal S at the terminals of the heating filament 15 is proportional to the concentration of the gas and therefore satisfies the following equation:

$$S = k \times C \tag{5}$$

in which k is the response coefficient or sensitivity of the system.

Thus, using the analogy previously referred to, the variation of the measuring signal S as a function of time during phase III is as follows:

$$S = kCs[r + 1(1-r)e^{-t/T}] \tag{6}$$

in which the coefficients k, r and T are the values proper to each inflammable gas for the analysis system shown in FIG. 1.

As previously mentioned, the value of the signal S varies as a function of the temperature of the heating element 15 and therefore has a wanted component dependent on the inflammable gas or gases of the gas mixture, in particular the concentration, and an unwanted component due to the value of the electrical supply current, the outside temperature, the moisture content of the air, the pressure, etc.

To eliminate the unwanted component, the central processor unit 30 compares two measurement points at measurement times $t_1$, and $t_2$ and generates the following signal L:

$$L(t1, t2) = S(t1) - S(t2) \tag{7}$$

From equation (6), the signal $$\overline{L} = \frac{L}{C_o}$$

satisfies the following equation:

$$\overline{L} = k(1 - \Delta C/Co)(1 r)(1 - e^{-\tau/T})e^{-t1/T} \tag{8}$$

in which:
- τ represents the difference between times $t_2$ and $t_1$,
- ΔC represents the drop in concentration during phase II, and
- Co represents the concentration of the or each inflammable gas in air.

As previously mentioned, in the presence of several inflammable gases of different kinds in the gas mixture filling the combustion chamber 14, each inflammable gas provides an individual signal S, the total signal consisting of the sum of all the individual signals.

To obtain reliable results, the central processor unit 30 and the synchronizing means 34 perform measurements in phase III at times $t_1$, and $t_2$ determined to obtain, for each inflammable gas, signals S which are substantially identical for concentrations corresponding to identical explosibilities.

This condition, establishing that the same concentrations of two gases m and i, expressed as a percentage of their lower explosibility limit (LEL), give the same signals, can be expressed as follows:

$$\overline{L}m \times (LEL)m = \overline{L}i \times (LEL)i \tag{9}$$

Thus, using equation (8), the above equation becomes:

$$\alpha i \times e^{(Ti - Tm) \cdot t_2 / TiTm} = \frac{e^{\tau/Tm} - 1}{e^{\tau/Ti} - 1} \tag{10}$$

in which:
αi = αexp.×αsens.×αreduc.×αinfl.
where:
αexp.=(LEL)i/(LEL)m; αsens.=ki/km; αreduc.=(1−r)i/(1−r)m;
αinfl.=[1−ΔC/Co]i/[1−ΔC/Co]m.

For example, for a mixture of methane and propane, in air, the following equation is obtained for a given enclosure:

$$0.92 e^{+0.230 t_2} = \frac{e^{\tau} - 1}{e^{0.720\tau} - 1} \tag{11}$$

In contrast, for a mixture to be analysed containing methane and hexane in air, equation (10) becomes:

$$0.64 e^{0.375 t_2} = \frac{e^{\tau} - 1}{e^{0.625\tau} - 1} \tag{12}$$

Figure 3:
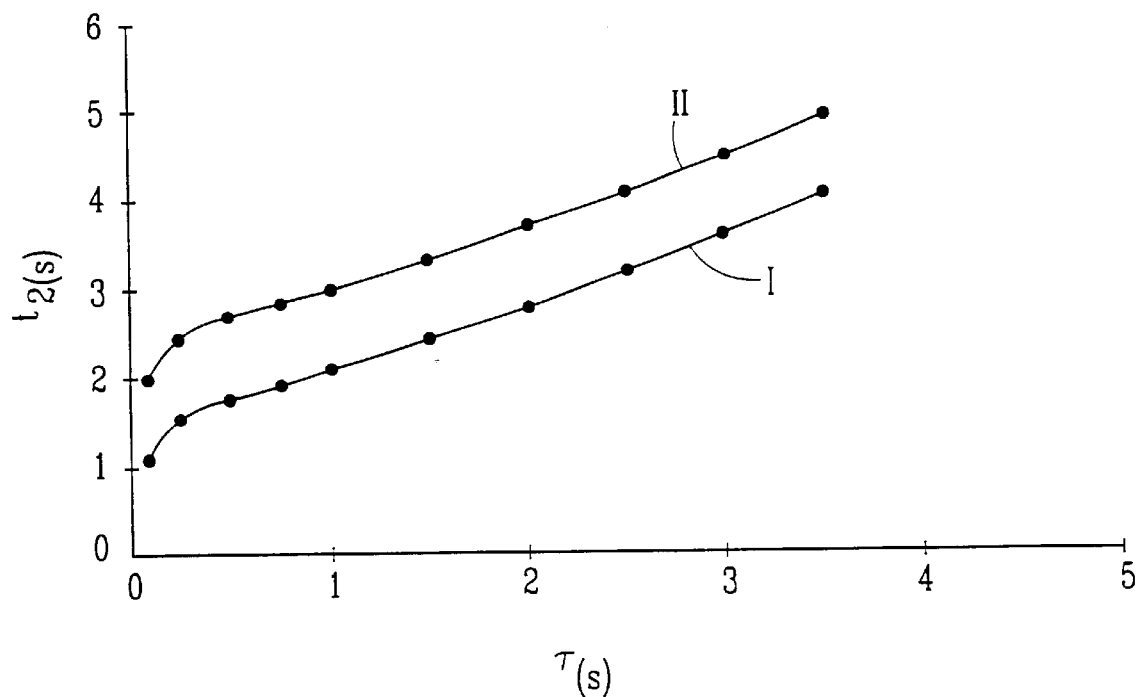
FIG. 3 is a curve showing the times for measuring the signal at the terminals of the resistive element to obtain identical signals for different inflammable gases at concentrations corresponding to the same explosibility.

FIG. 3 shows the variation of the second measuring time $t_2$ as a function of the difference τ between the measuring times $t_2$ and $t_1$, satisfying equations (11) and (12), respectively (curves I and II).

Thus, by choosing measuring times satisfying equation (10), the individual signals supplied to the analysis unit 24 are substantially identical for different inflammable gases having concentrations corresponding to identical explosibilities.

Note that the measuring times $t_1$, and $t_2$ preferably correspond to values of the measurement signal from around 80% to around 40% of the maximum value Ss of the electrical signal at the terminals of the filament 15. The measuring times can be refined for a given enclosure and as a function of the type of mixture by the optimization expressed by equations (9) and (10) and shown for three gases in FIG. 3.

In the foregoing description, the gas mixture was regarded as made up of a plurality of inflammable gases having relatively close combustion temperatures.

If one of the inflammable gases has a combustion regime or temperature very different from that of the other gases, the gas mixture is analysed by carrying out an analysis cycle specific to that gas. This applies to hydrogen in particular.

Figure 4:
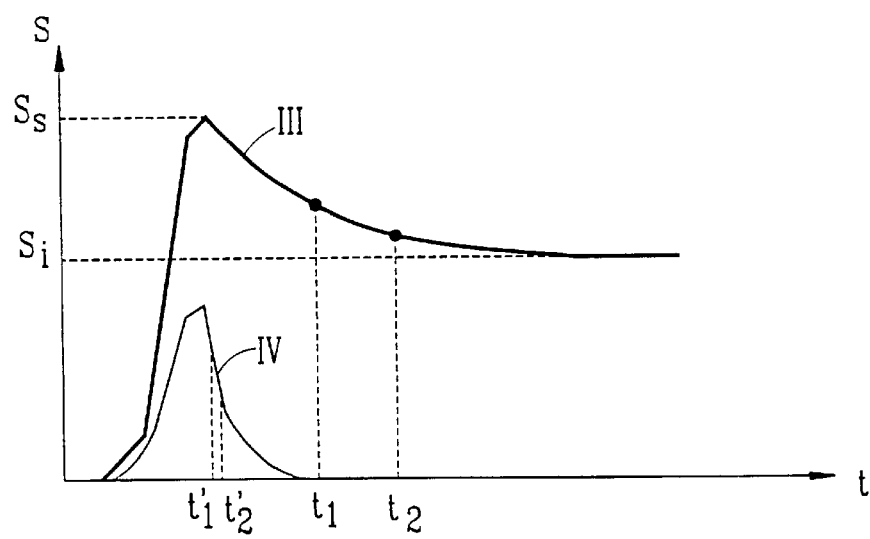
FIG. 4 is a curve showing one example of the variation as a function of time of the measurement signals for gases having very different combustion regimes.

FIG. 4 shows two curves III and IV respectively showing the variation as a function of time of the measurement signal S for a gas mixture containing hydrocarbons and for a gas mixture containing hydrogen. To analyse a mixture of these gases, the filament 15 is first heated to a first temperature, around 200° C. to burn only the hydrogen on the filament 15, and the explosibility of the gas mixture is determined, for hydrogen, as previously described, from two measurements carried out at times $t'_1$ and $t'_2$.

The temperature of the heating element 15 is then increased to a temperature corresponding to the combustion temperature of the other inflammable gases and the explosibility of the gas mixture is determined, for those other gases, as described above, using two measurements taken at times $t_1$ and $t_2$.

The explosibility of the gas mixture can therefore be obtained by adding the result supplied at the end of each analysis cycle.

For practical applications, the gas mixture is preferably analysed cyclically by energizing the filament 15 until the level Si is reached for the gas with the largest time constant T, after which the power supply is disconnected. The combustion chamber 14 then fills with gas to the point where the concentrations inside and outside the combustion chamber equalize, after which the filament 15 is energized again to perform a second measuring cycle.

By adapting the operating parameters of the system and the thermal inertia of the filament 15 it is possible to obtain a total cycle duration of a few seconds, which is satisfactory for most applications in the field of explosimetry.

Obviously the power consumption of the invention just described, which uses signals obtained by measuring the voltage at the terminals of a single heated filament to determine the risk of explosion of a gas, makes it particularly suitable for use as a portable device.

Furthermore, measuring errors can be considerably reduced by appropriately choosing the times to measure the voltage at the terminals of the filament so that the results obtained are identical for each inflammable gas in the mixture analysed for concentrations of those gases corresponding to identical percentages of the lower explosibility limit.

What is claimed is:

1. Method of analysing a gas mixture containing at least one inflammable gas to determine its explosibility, including the following steps:

energizing a resistive heating element (15) in an analysis enclosure (12) communicating with the gas mixture to be analysed to burn the gas mixture in the enclosure;

measuring an electrical signal (S) at the terminals of the resistive element (15) during combustion; and determining the explosibility of the gas mixture from a comparison of values of the signal measured during a transient phase in which the concentration of the inflammable gas or gases in the gas mixture is falling;

characterized in that the measurements taken during the transient phase are taken at times chosen to obtain, for different inflammable gases, substantially identical measurement signals for concentrations corresponding to identical explosibilities.

2. Method according to claim 1, characterized in that the analysis enclosure (12) has an inlet orifice (22) for the gas mixture calibrated to assure the diffusion of a quantity of gas towards the enclosure (12) during the transient phase which is less than the quantity of gas burned therein.

3. Method according to claim 2, characterized in that the measurements are taken at times corresponding to values of the measurement signal from approximately 80% to approximately 40% of the maximum value (Ss) of the electrical signal at the terminals of the resistive element (15).

4. Method according claim 3, characterized in that if the gas mixture includes a plurality of inflammable gases having different combustion regimes a cycle of analysing said mixture is performed for each inflammable gas by energizing the resistive element (15) to heat it to the combustion temperature of the gas, measuring the electrical signal (S) and determining the explosibility of the gas mixture, and the result obtained is added at the end of each analysis cycle.

5. Method according to claim 4, characterized in that the analysis enclosure (12) communicates with the gas mixture to be analysed via a porous partition (18).

6. Method according to claim 1, characterized in that the measurements are taken at times corresponding to values of the measurement signal from approximately 80% to approximately 40% of the maximum value (Ss) of the electrical signal at the terminals of the resistive element (15).

7. Method according to claim 1, characterized in that if the gas mixture includes a plurality of inflammable gases having different combustion regimes a cycle of analysing said mixture is performed for each inflammable gas by energizing the resistive element (15) to heat it to the combustion temperature of the gas, measuring the electrical signal (S) and determining the explosibility of the gas mixture, and the result obtained is added at the end of each analysis cycle.

8. Method according to claims 1, characterized in that the analysis enclosure (12) communicates with the gas mixture to be analysed via a porous partition (18).

9. System for analysing a gas mixture containing at least one inflammable gas to determine its explosibility, for implementing the method according to claim 1, characterized in that it includes an analysis enclosure (12) in communication with the gas mixture to be analysed and having a resistive heating element (15) disposed in an the internal volume of the enclosure (12) and a central analysis unit (24) including means (26) for energizing the resistive heating element (15) to heat it to the combustion temperature of the at least one inflammable gas, means (28) for calculating the explosibility of the gas mixture including means for measuring an electrical signal at the terminals of the heating element (15) and means for comparing values of the electrical signal at the terminals thereof, and in that the central analysis unit (24) includes means for controlling the operation of the measuring means so as to take said measurements during a transient phase of reduction of the concentration of the at least one inflammable gas in the gas mixture, at times chosen to obtain, for different inflammable gases, substantially identical measurement signals (S) for concentrations corresponding to identical explosibilities.

10. Analysis system according to claim 9, characterized in that the analysis enclosure (12) has a gas mixture inlet orifice (22), said orifice (22) being calibrated to assure the diffusion of a quantity of gas towards the enclosure (12) during the transient phase less than the quantity of gas burned therein.

11. System according to claim 10, characterized in that the analysis enclosure includes a combustion chamber (14) in which the resistive heating element (15) is disposed and an expansion chamber (16) communicating with the gas mixture to be analysed via a porous partition, a separator wall (20) incorporating said calibrated orifice (22) lying between the combustion chamber (19) and the expansion chamber (16).

* * * * *